United States Patent
Jussel

(10) Patent No.: US 8,317,512 B2
(45) Date of Patent: Nov. 27, 2012

(54) METHOD FOR OPERATING A FIRING FURNACE, IN PARTICULAR FOR THE DENTAL SECTOR, AND FIRING FURNACE

(75) Inventor: Rudolf Jussel, Feldkirch-Tosters (AT)

(73) Assignee: Ivoclar Vivadent AG, Schaan (LI)

( * ) Notice: Subject to any disclaimer, the term of this patent is extended or adjusted under 35 U.S.C. 154(b) by 976 days.

(21) Appl. No.: 11/975,479

(22) Filed: Oct. 20, 2007

(65) Prior Publication Data

US 2008/0096148 A1   Apr. 24, 2008

(30) Foreign Application Priority Data

Oct. 23, 2006   (DE) .......................... 10 2006 049 848

(51) Int. Cl.
  *F27B 9/12* (2006.01)
(52) U.S. Cl. .............................. 432/51; 432/18; 110/190
(58) Field of Classification Search ............... 432/4, 32, 432/49; 374/25
  See application file for complete search history.

(56) References Cited

U.S. PATENT DOCUMENTS

| | | | | |
|---|---|---|---|---|
| 3,655,941 A | * | 4/1972 | Schaun .......................... | 219/390 |
| 4,498,865 A | * | 2/1985 | Schulmeyer .................... | 432/18 |
| 4,796,688 A | * | 1/1989 | Gundlach et al. ............. | 164/457 |
| 4,983,811 A | * | 1/1991 | Oppor et al. ................... | 219/497 |
| 5,072,360 A | * | 12/1991 | Knorpp et al. ................. | 700/207 |
| 5,981,919 A | | 11/1999 | Masten, Jr. | |
| 6,324,341 B1 | * | 11/2001 | Riley et al. ..................... | 392/416 |
| 6,414,280 B1 | * | 7/2002 | Nishitani et al. ............... | 219/411 |
| 6,855,916 B1 | | 2/2005 | Matthews et al. | |
| 2002/0008334 A1 | | 1/2002 | Gheorghiu et al. | |
| 2004/0173142 A1 | * | 9/2004 | Willis ........................... | 117/200 |
| 2005/0204796 A1 | * | 9/2005 | Foser ............................ | 72/342.8 |
| 2010/0077941 A1 | * | 4/2010 | D'Agostini .................... | 110/188 |
| 2010/0077942 A1 | * | 4/2010 | D'Agostini et al. ........... | 110/205 |
| 2010/0077943 A1 | * | 4/2010 | Fogash et al. .................. | 110/215 |
| 2010/0077944 A1 | * | 4/2010 | Slavejkov et al. .............. | 110/345 |
| 2010/0077946 A1 | * | 4/2010 | D'Agostini .................... | 110/345 |

FOREIGN PATENT DOCUMENTS

| | | |
|---|---|---|
| DE | 28 56 304 A1 | 7/1980 |
| EP | 0 191 350 A2 | 8/1986 |

* cited by examiner

*Primary Examiner* — Steven B McAllister
*Assistant Examiner* — John Bargero
(74) *Attorney, Agent, or Firm* — Hodgson Russ LLP

(57) ABSTRACT

The invention relates to a method for operating a firing furnace, in particular for the dental sector, in which the temperature is measured and, based on the measured temperature, a temperature control is performed. If appropriate, the temperature integral, recorded at discrete points, is determined over the course of time and in particular stored, and is used, if appropriate in addition to the temperature, for controlling the firing furnace.

12 Claims, 2 Drawing Sheets

METHOD FOR OPERATING A FIRING FURNACE, IN PARTICULAR FOR THE DENTAL SECTOR, AND FIRING FURNACE

CROSS-REFERENCE TO RELATED APPLICATIONS

This application claims foreign priority benefits under 35 U.S.C. §119(a)-(d) from German patent application ser. no. 10 2006 049 848.8 filed Oct. 23, 2006.

TECHNICAL FIELD

The present invention relates to a method for operating a firing furnace, in particular for the dental sector, and to a corresponding firing furnace in which the temperature in the interior of the firing furnace is measured and, based on the measured temperature, the temperature in the interior of the furnace is measured and controlled and/or regulated.

BACKGROUND OF THE INVENTION

In dental firing furnaces, it is important for the temperature and also the so-called temperature profile, that is to say the course of the temperature over the course of time, to be maintained as precisely as possible, since the quality of the produced dental restoration parts, which can include casts, that is to say metal dental restoration parts, and also sintered parts, depends on this to a great extent.

In sintering operations in particular, the sinter conditions are crucial for achieving the desired material properties of the sintered dental material, which, for example, is pressed in a press furnace. These properties include the strength of the restoration, but also the translucence, especially in the case of crowns and ceramic veneers.

However, the temperature profile in the known dental firing furnaces greatly depends on various factors. Accordingly, it has long been known that the interference effects have to be compensated. Thus, for example, DE-A1 2,856,304 discloses a casting appliance for dental casts with a corresponding control device that can compensate for voltage fluctuations of the mains voltage, and thus provides a more uniform heating result.

It has also been known for some time to provide a temperature regulation, which nowadays is implemented in almost every dental firing furnace, and with which extremely precise regulation of the actual temperature to the setpoint temperature is achieved. To do so, it is necessary to compensate as far as possible for the stored energy in the thermal insulation and for the changing coil resistance of the heating coil, but also, for example, for the compound introduced into the muffle and for the associated temperature reduction.

In dental laboratories, but also in fairly large dental practices that use dental firing furnaces of this kind, it is desirable to achieve the lowest possible cycle time for production of a dental restoration.

It has been proposed to allow the firing furnace to heat up along a special heating curve which, with a very rapid temperature rise to a so-called overtemperature, initially heats the furnace for a certain time to a temperature that lies considerably above the processing temperature, that is to say the desired temperature at which the restoration part is to be processed. This method can also be referred to as overriding. With correct choice of the parameters (temperature, time), it does not damage the restoration part, since, because of the heat capacity of the muffle, the latter heats more quickly during the holding time of the overtemperature, but without reaching its processing temperature. Shortly before the processing temperature in the muffle is reached, the furnace temperature could be lowered to the processing temperature.

To achieve this, it has also been proposed to establish a so-called holding time during which the furnace is held at the overtemperature, while it is subsequently reduced by definition to the processing temperature.

Unfortunately, the thereby improved cycle time and the associated method have not proven themselves in tests. For various reasons, the ceramic is always damaged, presumably because of the overtemperatures, so that, despite the achieved improvement in the cycle time, furnaces of this kind are generally regarded as being difficult to control and risky.

To achieve an improvement in cycle time, without the furnace in question being able to damage the sinter ceramics, it has further been proposed to use a very high, but very brief heat impulse to achieve at least a certain reduction of the heating phase. However, this can only be done using specially equipped and particularly temperature-resistant furnaces in which it is possible, for example, to achieve a temperature of 1400°, instead of the typical overtemperature of 1150°, without damage to the furnace.

Typically, certain ceramics also have to be fired several times. Thus, it is known for a high-firing ceramic, that is to say a ceramic that is sintered for example in the temperature range between 900° C. and 940° C., to be fired first with a so-called dentine firing and, after cooling, for a so-called glaze firing to be applied thereon whose temperature is 20° C. lower, for example, than the temperature of the dentine firing. In firing procedures of this kind, which are still relatively common, two heating phases are thus needed, and this accordingly increases the significance of the heating phase for the overall quality.

OBJECTS AND SUMMARY OF THE INVENTION

The object of the invention is to make available a method for operating a firing furnace, in particular for dental ceramics, which is improved in terms of the cycle time, without there being any risk of the quality of the restoration being reduced, and with which restorations of uniform quality can be produced.

According to the invention, provision is made for an overtemperature which has a predetermined temperature profile and lies above the processing temperature in particular. However, the overtemperature according to the invention is not maintained for a predetermined holding time, as has already been proposed. Instead, a defined surface integral is calculated, namely the integral of the difference between actual furnace temperature and reference temperature, in particular a transformation temperature of a ceramic, insofar as this value is positive, integrated over time. As soon as a predetermined integral value, the so-called temperature-time surface, is reached, the device is switched off.

It is surprisingly found that, with the measure of establishing the temperature-time surface, various interference parameters can be automatically compensated: with reduced mains voltage, the temperature increase gradient of the heating time is less. It therefore takes longer for the overtemperature to be reached. According to the invention, instead of a predetermined holding time at the overtemperature, the temperature-time surface is now predetermined, which surprisingly leads to a muffle heating profile which is delayed only by a few seconds in relation to the optimal heating curve, but which does not show any overshoot at all. Damage to the restoration is thus reliably avoided, although the heating period is considerably shortened not only in the interference-free state, but in particular also in the case of interference, so that the cycle time as a whole.

It is true that it has already been proposed to program a metal casting furnace with a temperature control in such a way that an overheat temperature is implemented during the actual melting process, which overheat temperature is higher by a predetermined temperature difference than the end temperature. After expiry of a melt-time delay, the furnace is then regulated to the end temperature. However, this method does not take account of different error parameters, with the result that the aforementioned problems can likewise occur.

According to the invention, it is particularly expedient that, by establishing the difference integral as control variable for the temperature profile, the introduced heat capacity is also automatically included in the regulation. Thus, a larger muffle with an accordingly greater heat capacity causes a slower temperature increase in the interior of the furnace, which can be detected by a temperature sensor arranged there. The quantity of heat delivered is to this extent automatically adapted, it being understood that the actual regulation, that is to say the inner furnace control loop, can be implemented in a suitable manner, for example as PID controller.

It will also be appreciated that the furnace according to the invention can be calibrated in a manner known per se, preferably with a large muffle on the one hand and with a small muffle on the other hand, and the exact arrangement of the temperature sensor can also be established such that the error between the setpoint value and the actual value is as small as possible, specifically both in the case of the large muffle and also in the case of the small muffle, which as test muffle can be provided for example with an additional, inner temperature sensor that measures the actual temperature in the muffle.

In an advantageous embodiment, provision is made to control the temperature, particularly during the critical heating phase, via a microprocessor or microcontroller. The calculation of the difference integral, that is to say of the temperature-time surface, can then preferably be done numerically with discrete measured temperature values. The scanning rate can be adapted within wide limits to the particular requirements, with a scanning rate in the seconds range being sufficient in each case.

It will be appreciated that the firing furnace according to the invention can in principle be implemented in the narrower sense also as a press furnace. By virtue of the optimized temperature control, the cycle time can be minimized, although when using ceramics as firing material for a dental restoration the sintering can be done optimally. In terms of the heating phase, the firing furnace according to the invention also generally compensates automatically for an increase in the coil resistance of the heating coil and also takes account of the thermal energy stored in the heat insulation. Disturbance variables, such as the influence of the evacuation and renewed flooding of the firing chamber with air, can also be compensated according to the invention, as also can brief fluctuations of the mains voltage.

According to the invention, it is particularly expedient if the temperature control monitors the heating curve of the firing furnace and, if appropriate, corrects it.

According to the invention, it is particularly expedient if the firing furnace is heated by the temperature control to an overtemperature that lies above the processing temperature, and if the overtemperature is maintained during a holding time, then, if appropriate, the temperature control shortens the holding time.

According to the invention, it is particularly expedient if the integral is calculated above in particular the processing temperature.

According to the invention, it is particularly expedient if the integral is approximated from a multiplicity of discrete, measured temperature values.

According to the invention, it is particularly expedient if the temperature that is used for the regulation via the temperature control is measured on a regulating temperature sensor, in particular a thermocouple, which is spaced apart in particular from a press muffle that is fitted in the firing furnace.

According to the invention, it is particularly expedient if the setpoint temperature of the furnace, starting from a preheat temperature, is regulated to the overtemperature 10 with a predetermined temperature gradient and, after expiry of the holding time predetermined by the temperature control, is regulated from the overtemperature 10 to the processing temperature, in particular with a predetermined temperature gradient.

According to the invention, it is particularly expedient if the heating temperature gradient is steeper than the temperature gradient between the overtemperature 10 and the processing temperature 16.

According to the invention, it is particularly expedient if the integral of the furnace temperature, insofar as the latter exceeds the processing temperature 16, is determined over the course of time and is compared with a setpoint integral that corresponds to a setpoint quantity of delivered heat.

According to the invention, it is particularly expedient if the calculation of the integral is interrupted at the end of the holding time, corresponding to the departure from the overtemperature 10.

According to the invention, it is particularly expedient if the temperature control according to the invention entails, in addition to the actual regulation of the furnace temperature, the minimizing of the interval between actual temperature and setpoint temperature.

According to the invention, it is particularly expedient if the rising temperature gradient is monitored and, if it falls below a predetermined value, an alarm is output.

According to the invention, it is particularly expedient if the temperature control device records the temperature-time integral above in particular a processing temperature 16, and if the temperature control device heats the firing furnace to an overtemperature 10 that lies above the processing temperature 16, and the temperature control device maintains the firing furnace at this overtemperature 10 during a holding time.

According to the invention, it is particularly expedient if the firing furnace is designed as a press furnace.

BRIEF DESCRIPTION OF THE FIGURES

Further advantages, details and features will become clear from the following description of an illustrative embodiment of the invention with reference to the drawing, in which.

DETAILED DESCRIPTION

Figure 1:
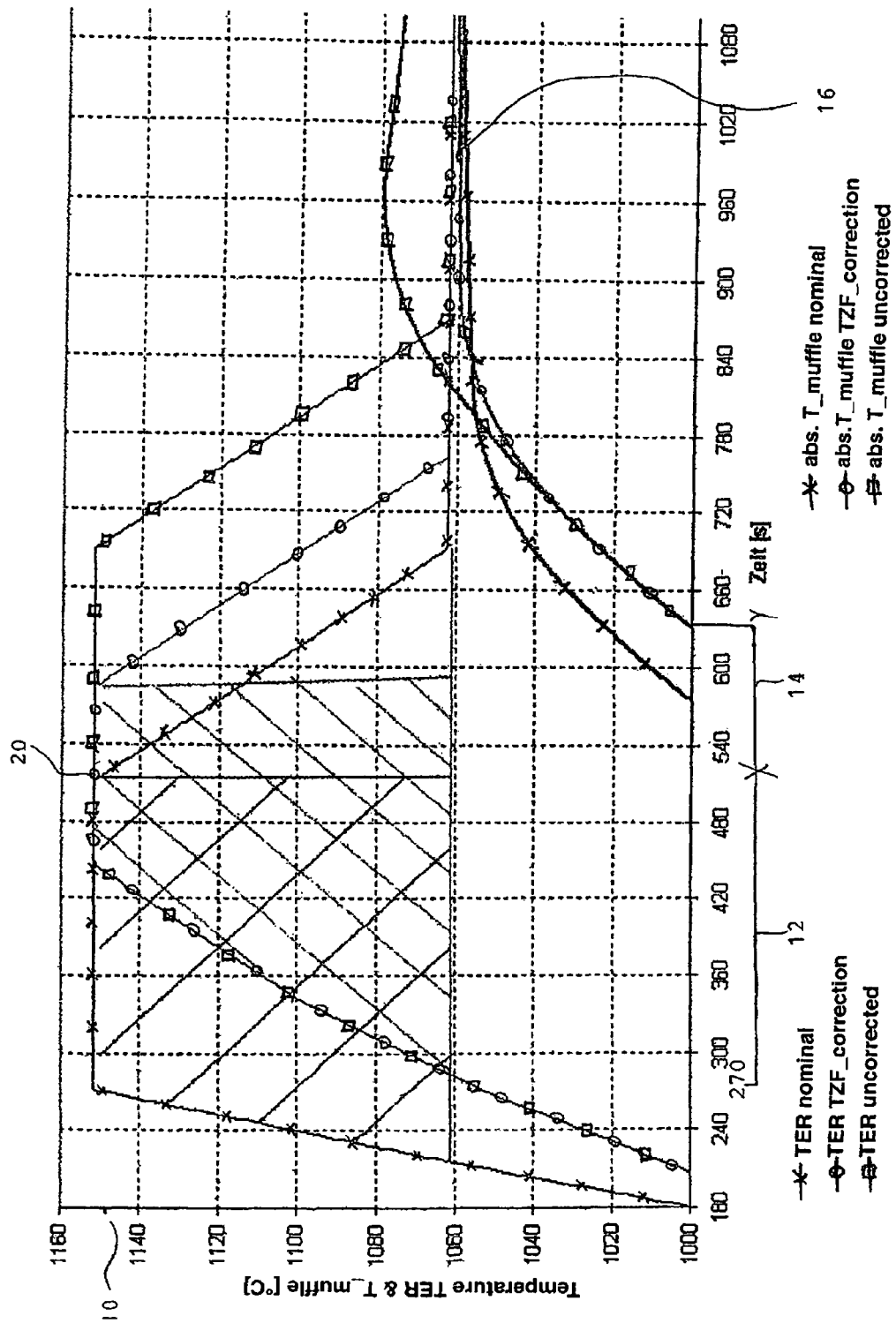
FIG. 1 shows a view of different temperature profiles to explain the operating method of a firing furnace according to the invention.

The temperature is plotted over time in FIG. 1, specifically during a heating period of the firing cycle of a firing furnace according to the invention in one embodiment. In the left-hand area of FIG. 1, the furnace temperature is shown in different temperature profiles, designated by TER, while the right-hand area shows the muffle temperature that was determined via a test muffle. This is designated by T_muffle.

Figure 2:
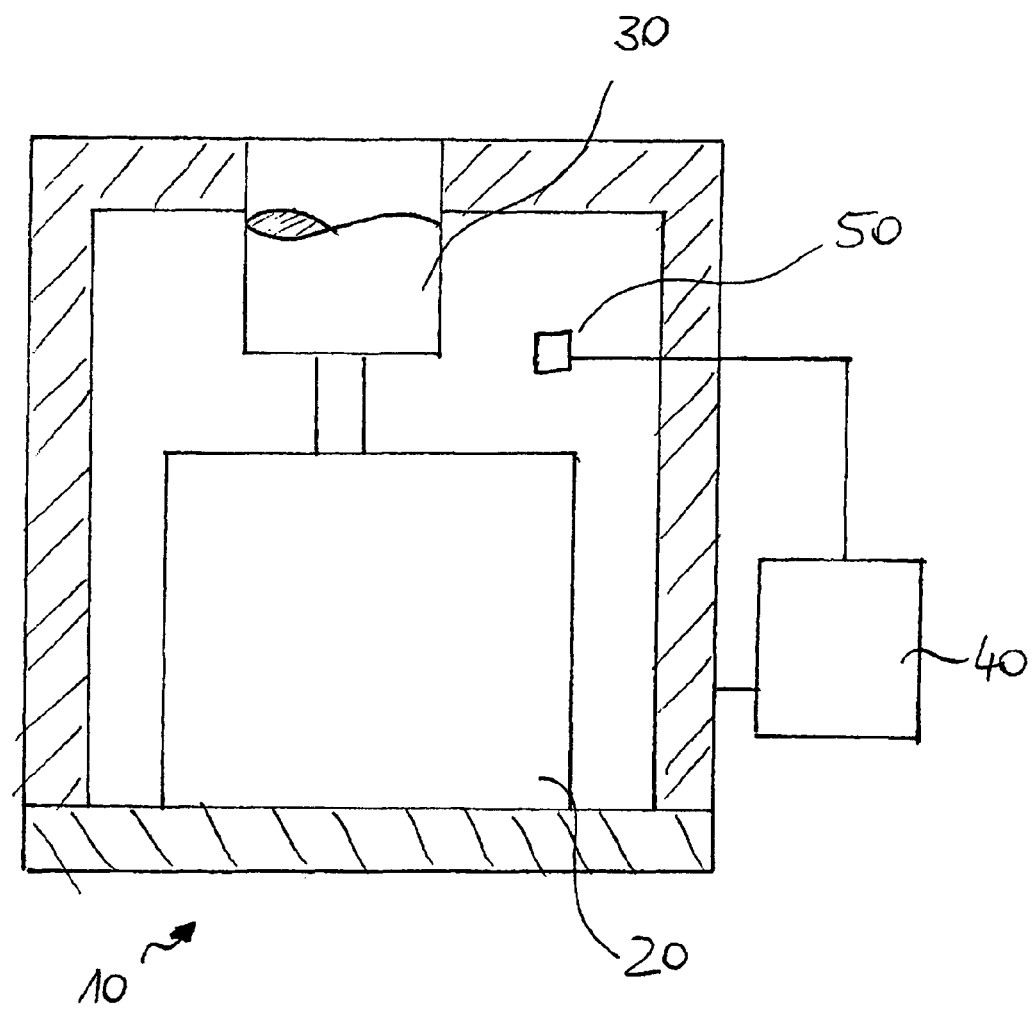
FIG. 2 is a somewhat schematic illustration of the apparatus of this invention.

In FIG. 2 the apparatus of this invention is illustrated. The apparatus includes a dental furnace 10 which has received a muffle 20. A press 30 contacts the muffle. In addition, control means 40 are interconnected with a thermal sensor in the form of a thermocouple 50.

A muffle is typically brought to a temperature of 800° C. or 850° C., for example, in a preheating furnace. When it is removed from the preheating furnace in order to be introduced into the firing furnace, the temperature typically drops, specifically in most cases by several tens of degrees, and a smaller muffle shows greater cooling than larger muffles. The start temperature in the firing furnace for the muffle in question is accordingly typically lower for a smaller muffle and higher for a larger muffle. However, the smaller muffle automatically heats up more, which to a certain extent compensates for this temperature difference.

In FIG. 1, the curve TER nominal indicates a furnace temperature that prevails in the firing furnace in the case where there is no error. As can be seen, the temperature rise from 1000° C. to about 1150° C. takes place with a strong temperature gradient of about 100° C./min. After the overtemperature 10 is reached, there is the nominal holding time 12 of four minutes. This is followed by a cooling phase 14 of approximately three minutes, until the processing temperature 16 of 1060° C. is reached.

The nominal muffle temperature arises from this heating temperature profile, as is shown in FIG. 1. During the heating time in which the furnace temperature lies significantly above the processing temperature 16, the muffle temperature is below 1040° C., that is to say below the processing temperature. According to the invention, a defined quantity of heat is delivered that, one the one hand, accelerates the heating of the muffle but, on the other hand, does not cause a temperature rise to above the processing temperature.

It will also be seen from FIG. 1 how the firing furnace reacts in the event of a disturbance. The assumed disturbance here is too low a mains voltage, which has the effect that the furnace receives too little power to achieve the desired rapid heating of the furnace temperature. In this case, the temperature profile TER TZF_correction arises. The temperature gradient is considerably less than 100° C./min and lies, for example, below the processing temperature 16 at 50° C./min. As the temperature further increases, the firing furnace no longer provides even this temperature gradient, so that, as the overtemperature 10 is approached, the temperature gradient may be only 30° C./min for example. This leads on the whole to significantly slower heating, so that the overtemperature 10 is reached only at about 450 seconds.

According to the invention, however, the holding time for the temperature is significantly shortened, specifically to just under 2½ minutes. This is normally followed by the cooling phase of 3 minutes.

According to the curve T_muffle TZF_correction, although this leads to a slightly delayed heating of the muffle, the temperature of the latter clearly never exceeds the processing temperature 16, so that no incorrect firing occurs.

According to the invention, this is ensured by calculating the difference integral of the furnace temperature over the course of time, if the furnace temperature exceeds the processing temperature. The integral is calculated until the switch-off time 20 of the overtemperature and is shown by hatching both for the nominal temperature and also for the furnace temperature TZF_correction. The corresponding temperature-time surfaces are equal, resulting in a reduced holding time according to the curve TZF_correction.

FIG. 1 also shows a temperature profile that is to be avoided according to the invention. Here, there is no compensation of the furnace error, so that the temperature rise corresponding to the temperature profile TZF_correction takes place as shown under TER uncorrected. This is followed by the holding time of 4 minutes, so that the switching off is effected at 690 seconds. At this point in time, the muffle temperature is approximately 1025° C., that is to say still considerably below the processing temperature 16. During the cooling phase of 3 minutes, however, the temperature exceeds the processing temperature, specifically just before the end, and surprisingly there is too high a temperature for a longer time, that is to say over 1080 seconds, and this causes lasting damage to the ceramic, as shown for T_muffle uncorrected.

The solution according to the invention completely avoids this damage in a surprisingly simple way and permits safe operation of a firing furnace despite a reduction in the cycle time.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A firing furnace for the dental sector, with a temperature control device via which the temperature in the interior of the furnace is measured and regulated, wherein the temperature control device determines the integral of the measured temperature over the course of time and stores it, the temperature control device recording the temperature-time integral above a processing temperature and, in addition to the measured recorded actual temperature, controls the firing furnace based on said integral, the temperature control device causing the firing furnace to be heated to an overtemperature that lies above the processing temperature, and the temperature control device maintaining the firing furnace at this overtemperature during a predetermined holding time and, wherein the temperature that is used for the regulation via the temperature control device is measured on a regulating temperature sensor in the form of one single thermocouple within the furnace, which is spaced apart in from a press muffle that is fitted in the firing furnace, and wherein the temperature is regulated along a predetermined temperature gradient to the processing temperature by the temperature control device.

2. The apparatus for operating a firing furnace as claimed in claim 1, wherein the temperature control device determines the integral at discrete points.

3. The apparatus for operating a firing furnace as claimed in claim 1,
wherein the temperature control monitors the heating curve of the firing furnace and, adjusts the temperature of the furnace.

4. The apparatus as claimed in claim 1, wherein the firing furnace is heated by the temperature control to an overtemperature that lies above the processing temperature, and wherein the overtemperature is maintained during a predetermined holding time, and the temperature control device shortens the predetermined holding time to maintain proper furnace temperatures.

5. The apparatus as claimed in claim 1, wherein the integral is calculated above the processing temperature.

6. The apparatus as claimed in claim 1, wherein the integral is approximated from a multiplicity of discrete, measured temperature values.

7. The apparatus as claimed in claim 1, wherein the integral of the furnace temperature, insofar as the latter exceeds the processing temperature, is determined over the course of time and is compared with a set-point integral that corresponds to a setpoint quantity of delivered heat.

8. The apparatus as claimed in claim 1, wherein the temperature control device according to the invention entails, in addition to the actual regulation of the furnace temperature, the minimizing of the interval between actual temperature and set-point temperature.

9. The apparatus as claimed in claim 1, wherein the rising temperature gradient is monitored and, if it falls below a predetermined value, an alarm is output.

10. The firing furnace as claimed in claim 1 wherein the firing furnace is designed as a press furnace.

11. A firing furnace for the dental sector, with a temperature control device via which the temperature in the interior of the furnace is measured and controlled and regulated, wherein the temperature control device determines the integral of the measured temperature over the course of time and stores it, and in addition to the recorded measured temperature controls the firing furnace based on said integral, and, wherein the temperature that is used for the regulation via the temperature control device is measured on a regulating temperature sensor in the form of a single thermocouple within the furnace, which is spaced apart from a press muffle that is fitted in the firing furnace, wherein the setpoint temperature of the furnace, starting from a preheat temperature is regulated to the overtemperature with a predetermined temperature gradient and, after expiry of a holding time predetermined by the temperature control device and, is regulated from the overtemperature to the processing temperature with a predetermined temperature gradient, and wherein the heating temperature gradient is steeper than the temperature gradient between the overtemperature and the processing temperature.

12. The apparatus as claimed in claim 11, wherein the calculation of the integral is interrupted at the end of the holding time, corresponding to the departure from the overtemperature.

* * * * *